United States Patent [19]

Regiroli et al.

[11] Patent Number: 4,522,825
[45] Date of Patent: Jun. 11, 1985

[54] ACARICIDE COMPOSITIONS EMPLOYING SYNERGISTIC MIXTURES OF 1-DECYLOXY-4-(7-OXA-4-OCTINYL)-OXY-BENZENE AND PROPARGITE

[75] Inventors: Giovanni Regiroli, Novate Milanese; Vincenzo Caprioli, San Martino; Angelo Longoni, Milan, all of Italy

[73] Assignee: Montedison S.p.A., Milan, Italy

[21] Appl. No.: 480,760

[22] Filed: Mar. 31, 1983

[30] Foreign Application Priority Data

Apr. 1, 1982 [IT] Italy ............................. 20526 A/82

[51] Int. Cl.³ ..................... A01N 37/52; A01N 41/02; A01N 55/04; A01N 57/00

[52] U.S. Cl. ..................... 514/517; 514/119; 514/189; 514/479; 514/493; 514/508

[58] Field of Search .......................................... 424/303

[56] References Cited

U.S. PATENT DOCUMENTS 4,307,115  12/1981  Klopping ............................ 424/327
4,388,323   6/1983  Massardo et al. ................... 424/341

Primary Examiner—Allen J. Robinson

[57] ABSTRACT

There are described mixtures with a synergistic action of two acaricide compounds as well as their use in suitable compositions in the fight against mite infestations on useful plants.

6 Claims, No Drawings

ACARICIDE COMPOSITIONS EMPLOYING SYNERGISTIC MIXTURES OF 1-DECYLOXY-4-(7-OXA-4-OCTINYL)-OXY-BENZENE AND PROPARGITE

The present invention concerns acaricide compositions and more particularly it relates to acaricide compositions containing as an active ingredient a mixture of two acaricide compounds developing a synergistic effect. The invention concerns, moreover, the use of such compositions in the protection of useful plants from infestations by mites.

In European Patent Application No. 37092 (Montedison S.p.A.), there have been described acaricide compounds endowed with a high activity developed mainly against mite eggs but also against adult mites.

Amongst these acaricides there is also the compound 1-decyloxy-4-[(7-oxa-4-octinyl)oxy]-benzene (henceforth indicated as compound A) of formula:

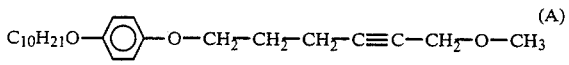

Compound A, as previously indicated, displays a high acaricide activity especially against mite eggs.

The acaricide activity of compound A is so high that its action on the mite eggs allows to disinfest in quite a satisfactory way the plants infested by mites.

It may, however, happen that under particular conditions of heavy infestation already widely diffused or occurring on plants of dense foliage wherefore it becomes difficult to reach the mite eggs with the treatment, the immediate efficacy of compound A proves reduced.

In general also in such cases within time there will practically occur a complete disinfestation thanks to the persistence of the acaricide action of compound A, but the high degree of contingent infestation may cause however considerable damage to the cultivations.

For this reason we have studied the possibility of combining compound A with a second acaricide compound endowed with an immediate action against adult mites.

The study of such mixtures has surprisingly evidenced how the combination of compound A with one of the hereunder indicated acaricides leads to an unforeseen increase in the acaricide activity in as much as the activity of the mixtures turns out to be greater than the sum of the activities of the single compounds at equal doses.

Thus, object of the present invention is that of providing mixtures developing synergistic acaricide activity and consisting of compound A and of an acaricide chosen from amongst the hereunder listed compounds, in a proportion comprised between 1:10 and 10:1 by weight.

The acaricides that may be used in combination with compound A in the mixtures object of this invention, are:

$B_1$—Tricyclohexyl-tin hydroxide (common name Cyhexatin)

$B_2$—Hexakis($\beta,\beta$-dimethylphenethyl)-distannoxane (common name Fenbutatin-oxide)

$B_3$—N-(4-chloro-o-tolyl)-N'N'-dimethylformamidine (common name Chlordimeform)

$B_4$—N'-(2,4-dimethylphenyl)-N-[(2,4-dimethylphenyl)-iminomethyl]-N-methylmethanimidamide (common name Amitraz)

$B_5$—4-chlorophenyl-4)chlorophenyl-sulphone (common name Chlorfenson)

$B_6$—2-(4-tert.butyl-phenoxy)-cyclohexyl-(2-propinyl)-sulphite (common name Propargite)

$B_7$—N,N-dimethyl-N'-[3-(methylaminocarbonyloxy)phenyl]-methanimidamide (common name Formetanate)

$B_8$—Ethyl-O-benzoyl-3-chloro-2,6-dimethoxy-benzohydroximate (common name Benzomate)

$B_9$—1,1-bis-(4-chlorophenyl)-2,2,2-trichloroethanol (common name Dicofol)

$B_{10}$—O,O-diethyl-S-(N-isopropylcarbamoylmethyl)-phosphorodithioate (common name Prothoate)

$B_{11}$—O,O-dimethyl-S-(N-methylcarbomoyl-methyl)-phosphorodithioate (common name Dimethoate)

$B_{12}$—Tricyclohexyl-(1,2,4-triazol-l-il)-tin (common name Azocyclotin).

Compounds $B_1$ to $B_{12}$ are known compounds that are commercialized as acaricides and some of them also as insecticides.

Further objects of this invention are acaricide compositions containing the synergistic mixtures of this invention and their use in the fight against mite infestations. The synergistic effect of the mixtures object of the present invention can be easily proved in laboratory tests in which it is possible to use separately suitable doses of compound A and of one of compounds B, so as to have a partial acaricide effect and detect the activity increase of the mixtures.

The field tests that have been carried out have evidenced an undoubted synergistic effect, even if difficult to be quantified just because of the practical character of the tests which also foresee possible re-infestation by mites that are foreign to the test conducted.

These results evidence quite clearly how the mixtures object of the present invention are suited for being used in the protection of plants against mite infestations.

The main mite species, of particular economical interest because of the damages caused to the plants and for their very wide diffusion over all cultivated areas, belong prevailingly to the families of: *Tetranychidae*, genera *Tetranychus* (*T. urticae, T. telarius, T. pacificus*, etc.), *Panonychus* (*P. ulmi, P. citri*, etc.), *Bryobia* (*B. praetiosa*) and *Oligonychus*.

Other species harmful to the cultivations are present for instance in the family *Eriophydae* (genera *Aceria, Eriophyes, Phylocoptes, Phyllocoptruta, Vasates*, etc.), and *Tenuipalpidae*.

Depending on the species, these mites are parassites of numerous cultivations, amongst which, for instance, fruit trees (particularly apple-tree, pear-tree, vine, peach-tree, apricot-tree and citrus fruit tree), horticultural cultivations, strawberries, tea, flower and ornamental plants, etc.

Thus, the acaricide mixtures object of the present invention are suited for numerous and diversified application both in agriculture as well as in floriculture.

Moreover, mixtures of the invention have also proved active against mites infesting foodstuffs, wherefore it is possible to use them in the protection of same.

For practical uses the mixtures object of the present invention may be used as such or preferably in the form of suitable compositions.

In the compositions, besides the synergistic mixture as the active principle, there may be also present solid or liquid inert carriers and optionally other additives such as surfactants, suspending agents, emulsifiers, dispersants, adhesive agents, etc.

According to the normal formulating practice, the compositions may be in the form of dry powders, wettable powders, pastes, concentrated emulsions, emulsifiable liquids, etc.

In the above said compositions the acaricide mixture may be contained in quantities comprised between 0.5 and 95% by weight depending on the type of compositions and on the particular use for which the compositions are intended.

The quantity of acaricide mixture to be spread over the area or onto the vegetation to be protected, depends on various different factors such as the type of composition used, the available applicative means, the nature and degree of infestation, the type of cultivation to be protected, on the climatic and environmental conditions.

In general, for an excellent protection of the cultivations from mite infestations, quantities of between 0.1 and 2 Kg/ha of acaricide mixture will be sufficient.

If desired, it is possible to prepare an extemporal mixture at the moment of treatment.

Since some of the compounds of type B are also endowed with an insecticide action, it is quite logical to expect that the mixtures of the invention will also show an insecticide activity.

To the described formulations there may optionally be added other active compatible substances chosen from amongst: insecticides, fungicides, phytoregulators, fertilizers, etc.

Since in European Patent Application No. 37092, previously cited, besides compound A there are also described other acaricide compounds with analogous properties, it will be likely that one may expect that also the other compounds described in above cited European Patent Application will show a synergistic effect when used in admixture with the acaricides from $B_1$ to $B_{12}$.

With the purpose of even better illustrating the present invention in the following there will be given a number of examples that will concern the acaricide activity and the synergistic effect of the mixtures object of this invention against mites of the *Tetranychus urticae* and *Panonychus ulmi* species. These mites are particularly representative for the damages they cause to the plants as well as for their wide diffusion.

EXAMPLE 1

Acaricide activity against *Tetranychus urticae*. The activity of the single compounds and of the mixtures against the above indicated mites has been determined according to the following procedure.

Small foliar discs obtained from bean leaves, of 4.5 cm diameter, have been infested with adult as well as young mites. After 12 days, that is once there was a mixed population of mobile forms and eggs, the test was started and one part of the discs was treated by sprinkling it, from a Potter tower, with a hydroacetonic solution (acetone=10% in volume) of the products or of the mixtures under examination. Another series of infested discs was treated only with the hydroacetonic mixture, without any active component, as a control.

The results were ascertained after 9 days from the day of treatment and the percentual effectiveness of the single compound or of the mixture was evaluated according to the following formula:

$$E\,(\%) = \left(1 - \frac{T_F \times C_I}{T_I \times C_F}\right) \cdot 100$$

wherein:
E (%)=percentual effectiveness;
$T_F$=number of mobile forms of mites at the end of the test on the treated discs;
$T_I$=number of mobile forms at the beginning of the test on discs to be treated;
$C_F$=number of mobile forms at the end of the test on the untreated discs (control);
$C_I$=number of mobile forms at the beginning of the test on the discs to be used as a control.

In the following Table 1 there have been recorded the data relating to the effectiveness of the single compounds at the tested doses.

TABLE 1

| Compound | Dose (mg/lt) | E (%) |
|---|---|---|
| A | 5 | 0 |
|   | 10 | 34 |
| $B_1$ | 2 | 18 |
|   | 5 | 50 |
| $B_2$ | 5 | 5 |
|   | 10 | 27 |
| $B_3$ | 5 | 0 |
|   | 10 | 14 |
| $B_4$ | 5 | 0 |
|   | 10 | 29 |
| $B_5$ | 50 | 0 |
|   | 100 | 17 |
| $B_6$ | 2 | 3 |
|   | 5 | 27 |
| $B_7$ | 50 | 15 |
|   | 100 | 42 |
| $B_8$ | 50 | 8 |
|   | 100 | 44 |
| $B_9$ | 10 | 10 |
|   | 50 | 31 |
| $B_{10}$ | 5 | 13 |
|   | 10 | 35 |
| $B_{11}$ | 5 | 5 |
|   | 10 | 29 |
| $B_{12}$ | 2 | 14 |
|   | 5 | 46 |

On following Table 2 have been recorded the data relating to the acaricide effectiveness observed in the mixtures compared to the activity expected in the case of simple additive properties.

TABLE 2

| Effectiveness of the mixtures against *T. urticae*. | | | | | |
|---|---|---|---|---|---|
| Mixture | Dose A | Dose B | Ratio by weight A:B | (1) $E_A + E_B$ (%) | (2) $E_M$ (%) |
| A + $B_1$ | 5 | 2 | 2.5:1 | 18 | 63 |
|   | 5 | 5 | 1:1 | 50 | 84 |
|   | 10 | 5 | 2:1 | 84 | 100 |
| A + $B_2$ | 5 | 10 | 1:2 | 27 | 45 |
|   | 10 | 10 | 1:1 | 61 | 89 |
|   | 10 | 5 | 2:1 | 39 | 59 |
| A + $B_3$ | 5 | 10 | 1:2 | 14 | 25 |
|   | 10 | 10 | 1:1 | 48 | 87 |
|   | 10 | 5 | 2:1 | 34 | 56 |
| A + $B_4$ | 5 | 10 | 1:2 | 29 | 50 |
|   | 10 | 10 | 1:1 | 63 | 91 |
|   | 10 | 5 | 2:1 | 34 | 58 |
| A + $B_5$ | 10 | 50 | 1:5 | 34 | 53 |
|   | 10 | 100 | 1:10 | 51 | 76 |
| A + $B_6$ | 5 | 2 | 2.5:1 | 3 | 33 |
|   | 5 | 5 | 1:1 | 27 | 60 |
|   | 10 | 5 | 2:1 | 61 | 96 |
| A + $B_7$ | 10 | 50 | 1:5 | 49 | 90 |

TABLE 2-continued

Effectiveness of the mixtures against *T. urticae.*

| Mixture | Dose A | Dose B | Ratio by weight A:B | (1) $E_A + E_B$ (%) | (2) $E_M$ (%) |
|---|---|---|---|---|---|
|         | 10 | 100 | 1:10 | 76 | 100 |
| A + B$_8$ | 10 | 50  | 1:5  | 42 | 57  |
|         | 10 | 100 | 1:10 | 78 | 91  |
| A + B$_9$ | 5  | 10  | 1:2  | 10 | 43  |
|         | 10 | 10  | 1:1  | 44 | 76  |
|         | 10 | 50  | 1:5  | 65 | 90  |
| A + B$_{10}$ | 5 | 5  | 1:1 | 13 | 35 |
|         | 5  | 10  | 1:2  | 35 | 79  |
|         | 10 | 5   | 2:1  | 47 | 92  |
| A + B$_{11}$ | 5 | 5  | 1:1 | 5  | 25 |
|         | 5  | 10  | 1:2  | 29 | 65  |
|         | 10 | 5   | 2:1  | 39 | 78  |
| A + B$_{12}$ | 5 | 2  | 2.5:1 | 14 | 53 |
|         | 5  | 5   | 1:1  | 46 | 75  |
|         | 10 | 5   | 2:1  | 80 | 100 |

Notes to Table 2:
(1) The values of the effectiveness of each product have been recorded on Table 1.
(2) $E_M$ = effectiveness observed of the mixtures.

EXAMPLE 2

Acaricide activity against *Panonychus ulmi.*

The acaricide activity of the single compounds and of the mixtures against the above indicated mites has been evaluated according to the following methodology.

Small discs of 4.5 cm diameter, obtained from apple-tree leaves, were infested with adult mites and juvenile forms of the same.

The test was started 12 days after the day of infestation, that is, when on the discs would be observed the presence of a mixed population of mites consisting of mobile forms and of eggs.

One part of infested discs was treated by sprinkling it, from a Potter tower, with a hydroacetonic solution (acetone=10% by volume) of the products or mixtures under examination.

Another series of infested foliar discs was treated only with the hydroacetonic solution, as a control.

The results were taken 9 days after treatment and the percentual effectiveness of the single compound or of the mixture was evaluated according to the following formula:

$$E\,(\%) = \left(1 - \frac{T_F \times C_I}{T_I \times C_F}\right) \cdot 100$$

wherein:
E (%)=percentual effectiveness.
$T_F$=number of mobile forms of mites at the end of the test on the treated discs.
$T_I$=number of mobile forms at the beginning of the test on the treated discs.
$C_F$=number of mobile forms at the end of the test on the untreated discs (control).
$C_I$=number of mobile forms at the beginning of the test on the discs to be used as controls.

In the following Table 3 there have been recorded the data relating to the effectiveness of the single compounds at the tested doses.

TABLE 3

Effectiveness of the single compounds against *P. ulmi.*

| Compound | Dose (mg/lt) | E (%) |
|---|---|---|
| A | 5 | 0 |
|   | 10 | 31 |
| B$_1$ | 2 | 10 |
|   | 5 | 49 |
| B$_2$ | 5 | 0 |
|   | 10 | 25 |
| B$_3$ | 5 | 0 |
|   | 10 | 7 |
| B$_4$ | 5 | 0 |
|   | 10 | 18 |
| B$_5$ | 50 | 0 |
|   | 100 | 0 |
| B$_6$ | 2 | 0 |
|   | 5 | 21 |
| B$_7$ | 50 | 10 |
|   | 100 | 38 |
| B$_8$ | 50 | 15 |
|   | 100 | 49 |
| B$_9$ | 10 | 0 |
|   | 50 | 27 |
| B$_{10}$ | 5 | 7 |
|   | 10 | 21 |
| B$_{11}$ | 5 | 0 |
|   | 10 | 18 |
| B$_{12}$ | 2 | 7 |
|   | 5 | 38 |

In the following Table 4 have been recorded the data relating to the observed acaricide effectiveness of the mixtures in comparison with the activity expected in the case of simple additive properties.

TABLE 4

Effectiveness of the mixtures against *P. ulmi.*

| Mixture | Dose A mg/lt | Dose B mg/lt | Ratio by weight A:B | (1) $E_A + E_B$ (%) | (2) $E_M$ (%) |
|---|---|---|---|---|---|
| A + B$_1$ | 5 | 2 | 2.5:1 | 10 | 55 |
|  | 5 | 5 | 1:1 | 49 | 87 |
|  | 10 | 5 | 2:1 | 80 | 100 |
| A + B$_2$ | 5 | 10 | 1:2 | 25 | 38 |
|  | 10 | 10 | 1:1 | 56 | 70 |
|  | 10 | 5 | 2:1 | 31 | 49 |
| A + B$_3$ | 5 | 10 | 1:2 | 7 | 28 |
|  | 10 | 10 | 1:1 | 38 | 85 |
|  | 10 | 5 | 2:1 | 31 | 80 |
| A + B$_4$ | 5 | 10 | 1:2 | 18 | 23 |
|  | 10 | 10 | 1:1 | 49 | 85 |
|  | 10 | 5 | 2:1 | 31 | 71 |
| A + B$_5$ | 10 | 50 | 1:5 | 31 | 58 |
|  | 10 | 100 | 1:10 | 31 | 79 |
| A + B$_6$ | 5 | 2 | 2.5:1 | 0 | 35 |
|  | 5 | 5 | 1:1 | 21 | 51 |
|  | 10 | 5 | 2:1 | 52 | 88 |
| A + B$_7$ | 10 | 50 | 1:5 | 41 | 79 |
|  | 10 | 100 | 1:10 | 69 | 100 |
| A + B$_8$ | 10 | 50 | 1:5 | 46 | 80 |
|  | 10 | 100 | 1:10 | 80 | 100 |
| A + B$_9$ | 5 | 10 | 1:2 | 0 | 37 |
|  | 10 | 10 | 1:1 | 31 | 51 |
|  | 10 | 50 | 1:5 | 58 | 84 |
| A + B$_{10}$ | 5 | 5 | 1:1 | 7 | 29 |
|  | 5 | 10 | 1:2 | 21 | 71 |
|  | 10 | 5 | 2:1 | 38 | 89 |
| A + B$_{11}$ | 5 | 5 | 1:1 | 0 | 21 |
|  | 5 | 10 | 1:2 | 18 | 58 |
|  | 10 | 5 | 2:1 | 31 | 74 |
| A + B$_{12}$ | 5 | 2 | 2.5:1 | 7 | 37 |
|  | 5 | 5 | 1:1 | 38 | 66 |
|  | 10 | 5 | 2:1 | 69 | 92 |

Notes to Table 4:
(1) The values of the effectiveness of the single products have been recorded on Table 3.
(2) $E_M$ = observed effectiveness of the mixture.

What we claim is:
1. An acaricide mixture with synergistic effect consisting of a mixture of the compound 1-decyloxy-4-(7- oxa-4-octinyl)-oxy-benzene with 2-(4-tert.butyl-phenoxy)-cyclohexyl-(2-propinyl-sulphite, in a ratio of 2.5:1 and 1:1.

2. An acaricide composition comprising an acaricidally effective amount of the synergistic mixture of claim 1 and an inert carrier.

3. A method for combatting mite infestations on plants of agricultural interest or of ornamental character consisting of distributing on the plants an acaricidally effective amount of a composition according to claim 2.

4. The method according to claim 3, wherein the mites belonging to the *Tetranychidae* family.

5. The method according to claim 3, wherein the mites belonging to the *Tetranychus* family.

6. The method according to claim 3, wherein the mites belonging to the *Panonychus* family.

* * * * *